(12) United States Patent
Knoche (10) Patent No.: US 7,358,081 B2
(45) Date of Patent: Apr. 15, 2008

(54) DEVICES FOR THE ELECTROCHEMICAL DETECTION OF A NUCLEOTIDE SEQUENCE, ANALYSIS CASSETTES, SYSTEMS OF ANALYSIS CASSETTES, SUPPLEMENTAL MODULES, AND METHODS FOR PRODUCING ANALYSIS CASSETTES

(75) Inventor: Jochem Knoche, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 500 days.

(21) Appl. No.: 10/384,210

(22) Filed: Mar. 6, 2003

(65) Prior Publication Data
US 2003/0199080 A1   Oct. 23, 2003

(30) Foreign Application Priority Data
Mar. 7, 2002   (DE) .................. 102 10 051

(51) Int. Cl.
*C12M 3/00*   (2006.01)
*C12Q 1/68*   (2006.01)
*G06F 13/12*  (2006.01)
*G06F 13/38*  (2006.01)

(52) U.S. Cl. ............... 435/287.2; 435/283.1; 435/6; 710/69

(58) Field of Classification Search ............. None
See application file for complete search history.

(56) References Cited

U.S. PATENT DOCUMENTS

| | | | | |
|---|---|---|---|---|
| 4,911,794 A | * | 3/1990 | Parce et al. ............ | 205/778 |
| 5,312,527 A | | 5/1994 | Mikkelsen et al. | |
| 5,470,534 A | * | 11/1995 | Imai et al. ............. | 422/67 |
| 5,641,004 A | * | 6/1997 | Py ...................... | 141/3 |
| 5,776,672 A | | 7/1998 | Hashimoto et al. | |
| 5,849,486 A | * | 12/1998 | Heller et al. ........... | 435/6 |
| 5,866,430 A | * | 2/1999 | Grow .................... | 436/172 |

(Continued)

FOREIGN PATENT DOCUMENTS

DE   199 40 647 A1   3/2001

(Continued)

OTHER PUBLICATIONS

Edelstein et al., Biosensors and Bioelectronics, vol. 14, pp. 805-813 (2000).*

(Continued)

*Primary Examiner*—Jehanne Sitton
*Assistant Examiner*—Robert T Crow
(74) *Attorney, Agent, or Firm*—Brinks, Hofer, Gilson & Lione (57) ABSTRACT

Devices for the electrochemical detection of a nucleotide sequence in a fluid are described that include (a) a working electrode and a counter-electrode wherein the working electrode is attached to a biopolymer that has a specific affinity with the nucleotide sequence to be detected; (b) an exchangeable analysis cassette for introducing the fluid wherein the working electrode and the counter-electrode are arranged in the analysis cassette and can be contacted with the fluid; (c) a portable computer arrangement electrically connected with the analysis cassette containing a display and an energy source independent of an electrical supply net and (d) a temperature-regulating element for cooling and/or heating the fluid in the cassette, which is fed from the energy source. Analysis cassettes, systems of analysis cassettes, supplemental modules, and methods for producing analysis cassettes are also described.

24 Claims, 7 Drawing Sheets

U.S. PATENT DOCUMENTS

| | | | |
|---|---|---|---|
| 5,871,918 A | | 2/1999 | Thorp et al. |
| 5,942,443 A | * | 8/1999 | Parce et al. ............... 436/514 |
| 5,972,692 A | | 10/1999 | Hashimoto et al. |
| 6,054,277 A | * | 4/2000 | Furcht et al. ............... 435/6 |
| 6,063,259 A | | 5/2000 | Wang et al. |
| 6,116,257 A | * | 9/2000 | Yokota et al. ............... 137/1 |
| 6,159,681 A | * | 12/2000 | Zebala ............... 435/4 |
| 6,264,825 B1 | * | 7/2001 | Blackburn et al. ....... 205/777.5 |
| 2001/0010917 A1 | | 8/2001 | Bertling |
| 2001/0021534 A1 | * | 9/2001 | Wohlstadter et al. ....... 436/518 |

FOREIGN PATENT DOCUMENTS

| | | |
|---|---|---|
| WO | WO 95/12808 | 10/1994 |
| WO | WO 97/12063 | 9/1996 |
| WO | WO 98/05958 | 7/1997 |
| WO | WO 01/42508 A2 | 12/2000 |
| WO | WO01/16361 A2 | 3/2001 |
| WO | WO01/16361 A2 | 3/2001 |

OTHER PUBLICATIONS

Golden et al., Opt. Eng., vol. 36, pp. 1008-1013 (1997).*

"From Polarography of DNA to Microanalysis with Nuclic Acid0Modified Electrodes", by Emil Palecek; VCH Verlagsgesellschaft mbH. D-69469 Weinheim, 1996—Electroanalysis 1996 8, No. 1; pp. 7-14.

* cited by examiner

DEVICES FOR THE ELECTROCHEMICAL DETECTION OF A NUCLEOTIDE SEQUENCE, ANALYSIS CASSETTES, SYSTEMS OF ANALYSIS CASSETTES, SUPPLEMENTAL MODULES, AND METHODS FOR PRODUCING ANALYSIS CASSETTES

REFERENCE TO RELATED APPLICATIONS

The present patent document claims priority to German Application Serial No. DE 10210051.9, filed Mar. 7, 2002, which is hereby incorporated by reference.

BACKGROUND

The present invention relates to devices for the electrochemical detection of nucleotide sequences in fluids, to analysis cassettes for use therewith, and to methods of producing analysis cassettes.

A device for measuring ion concentrations is described in DE 41 39 121 C1, which has a measuring insert that can be inserted into a base device in an exchangeable manner. For this purpose, the fluid to be tested is placed into the measuring insert. A device for the interchangeable reception of measuring cartridges or measuring cells for the determination of biochemical measurement parameters is described in WO 98/05958. The device is connected with a computer-controlled analysis system.

In the field of medical technology, it is possible to detect various illnesses or faulty developments by detecting genetically significant traces caused by the illness or faulty development in a bodily fluid or tissue. For example, pathogenic bacteria or viruses leave behind broken pieces of their DNA (i.e. nucleotides or sequences thereof) in the blood or urine; these are nucleotide sequences, oligo-nucleotide sequences or poly-nucleotide sequences. With various types of cancerous diseases it is possible to detect portions of the diseased cancer cells with their genetically significant defects in bodily fluids. Similar types of problems arise in the field of food chemistry, where the aim is to identify the bacteria responsible for the spoilage of food by detecting corresponding genetically significant traces. The detecting of genetic traces also occurs in the course of testing food to identify source, in particular in order to obtain information whether components contained in the food stem from natural plants or genetically manipulated plants.

In accordance with a known process, blood is taken from a patient, and an anticoagulant as well as a substance which breaks open cell walls are added thereto. Added to this is a special enzyme, which cuts the DNA strands released after the cell walls have been broken open at exactly predetermined locations ("enzymatic scissors").

Following this first step, a polymerase chain reaction (PCR) is generally performed in a second step in order to increase the sensitivity for the subsequent detection step. Such a method is described in DE 198 26 153 A1. A replication or multiplication of the DNA segments contained in the solution or fluid is stimulated by the polymerase chain reaction. The molecular elements required for this, which are the four amino acids contributing to the composition of the DNA, are added to the specimen. Then the specimen is heated in a controlled manner and cooled again thereafter. The detection process, i.e. the third step, is performed by a fluorescence-based method.

Electrochemical methods for detecting DNA segments are also known (e.g., German laid-open, non-examined Patent Application no. 199 40 647 A1, U.S. Pat. Nos. 5,312,527 and 5,871,918). Moreover, electrochemical detection methods are described in WO 01/42508 A2 and WO 95/12808. The system disclosed in the last mentioned document is very elaborate and can only be used efficiently in a large laboratory.

In accordance with electrochemical detection systems, the DNA segments or nucleotide sequences in question are detected in the solution by special working electrodes, which have been coated with special receptor molecules or biopolymers (i.e., with matching "counter pieces" to the DNA segments or nucleotide sequences in question). Only the exactly matching nucleotide sequences settle on the working electrode inserted into the fluid, so that this settling can subsequently be detected by an electrical evaluation.

A method used in this regard is PSA (potentiometric stripping analysis). In this method, a current is applied between the working electrode and a counter electrode. A slowly rising voltage can then be measured between the working electrode and a reference electrode. If nucleotide sequences of the type in question have settled on the working electrode, a stop of the voltage increase can be observed at a defined value (e.g., at 0.8 V) since at this voltage the guanine contained in the DNA segment in question, for example, is oxidized. The chronological width of this voltage plateau can be used as the measure of the amount of oxidized guanine, from which a conclusion can be drawn as to whether DNA segments of the type in question were present in a diagnostically relevant amount in the tested specimen.

The devices used with such process steps are devices used in laboratory chemistry. Because of their size, they are only suited for stationary employment. As a rule, the devices contain expensive components for transporting and metering the fluid and for the subsequent cleaning of the analysis chamber. The components include storage containers, valves, hoses, pumps, and the like. This use of such devices typically demands large space requirements. Moreover, the components require a considerable outlay for maintenance, since the demands made on cleanliness of the fluids are at a high level. Since the devices customarily used can only be used in a laboratory, respective specimens must often be transported first to a remote central laboratory. This is a great disadvantage, in particular for medical science in connection with acute illnesses.

SUMMARY

The scope of the present invention is defined solely by the appended claims, and is not affected to any degree by the statements within this summary.

A device for the electrochemical detection of a nucleotide sequence in a fluid embodying features of the present invention includes (a) a working electrode and a counter-electrode wherein the working electrode is attached to a biopolymer that has a specific affinity with the nucleotide sequence to be detected; (b) an exchangeable analysis cassette for introducing the fluid wherein the working electrode and the counter-electrode are arranged in the analysis cassette and can be contacted with the fluid; (c) a portable computer arrangement electrically connected with the analysis cassette containing a display and an energy source independent of an electrical supply net, wherein at least one of a voltage and a current can be impressed on at least one of the working electrode and the counter-electrode; wherein at least one of a current and a voltage signal can be detected as a consequence of the nucleotide sequence to be detected being deposited on the working electrode; and wherein a detection result can be represented on the display; and (d) a temperature-regulating element for cooling and/or heating the fluid in the cassette, which is fed from the energy source.

An analysis cassette for the electrochemical detection of a nucleotide sequence in a fluid embodying features of the present invention includes a sealed housing in which a working electrode and a counter-electrode are arranged. The working electrode has a biopolymer attached thereto, which has a specific affinity with the nucleotide sequence to be detected. The housing has a feeding device for conveying the fluid to at least one of the working electrode and the counter electrode in the housing.

A system of analysis cassettes embodying features of the present invention includes a plurality of analysis cassettes. Each analysis cassette of the plurality contains at least one working electrode for detecting at least one nucleotide sequence. The analysis cassettes differ from one another in that each is configured for detecting at least one of a particular nucleotide sequence and a combination of nucleotide sequences, wherein the particular nucleotide sequence and the combination of nucleotide sequences differ from one another.

A supplemental module for connection with a digital interface of a portable computer embodying features of the present invention includes an analog interface for connection with an exchangeable analysis cassette including (a) an electronic circuit arrangement configured for impressing at least one of a voltage and a current on at least one of a working electrode, a counter-electrode, and a reference electrode in the analysis cassette, and for conditioning at least one of a current and a voltage signal created as a result of an electrochemical reaction in the analysis cassette, and (b) a temperature-regulating element for cooling and/or heating a fluid introduced into the analysis cassette, wherein the supplemental module can be connected to the portable computer such that the temperature-regulating element can be fed from an energy source of the computer.

A method for producing an analysis cassette embodying features of the present invention includes (a) producing a molded plastic part; (b) connecting a plurality of working electrodes to the molded plastic part; (c) connecting a plurality of counter-electrodes to the molded plastic part; (d) contacting at least one of the working electrodes with at least one of a plurality fluids, wherein the fluids comprise a biopolymer; (e) folding the molded plastic part such that each of the working electrodes is positioned above the counter-electrode associated therewith; and (f) connecting wall elements of the plastic molded part which come to rest on each other by a technique selected from the group consisting of gluing and welding, thereby forming a sealed housing of the analysis cassette.

DETAILED DESCRIPTION OF THE PRESENTLY PREFERRED EMBODIMENTS

A device for the electrochemical detection of a nucleotide sequence has been discovered which can be employed at the site where a specimen is taken, for example at the location of the patient (the so-called "point of care"), which provides a detection result directly. In addition, aids and production methods for aids which permit cost-effective device production to enable large-scale production for decentralized use have also been discovered.

A device in accordance with the invention includes (a) an exchangeable analysis cassette for introducing fluid, wherein the working electrode and the counter-electrode are arranged in the analysis cassette and can be brought into contact with the fluid; (b) a portable computer arrangement, which can be electrically connected with the analysis cassette and which has a display and an energy source independent of the electrical supply net, wherein the computer arrangement is designed in such a way that a voltage and/or a current can be impressed on the electrodes, that a current and/or voltage signal as a consequence of the deposition of the nucleotide sequence to be detected on or at or in the working electrode can be detected, and that a detection result on the basis of this can be represented on the display; and (c) a temperature-regulating element, which is being fed from the energy source, for cooling and/or heating the fluid in the cassette.

As used herein, a portable computer arrangement is understood to be any computer arrangement which is intended for mobile employment, for example a laptop, notebook, palmtop or "hand-held" device.

It has been discovered that the electrochemical detection methods described above can be performed using a portable device (e.g., PCR and PSA can be performed in a decentralized manner).

Moreover, devices in accordance with the invention avoid active components for transporting, recirculating or metering the fluid. Instead, an exchangeable analysis cassette is provided, which is preferably designed as an expendable cassette in the form of an expendable or consumable article. Thus, the requirement for regular cleaning and/or maintenance of respective components is avoided. By the analysis cassette on the one hand, and the computer arrangement on the other hand, a device in accordance with the invention is divided in a functionally advantageous manner into an exchangeable wet element ("chemical module") and an electrical element which can be used over a long run.

In accordance with the invention, it is possible in an advantageous manner even for a user who has not been specially trained in laboratory chemistry to detect nucleotide sequences electrochemically at the location of the patient, or in the course of taking a chemical food specimen. The time needed for transporting specimens to a central laboratory can be omitted. This also enables a considerable cost savings.

With the temperature-regulating element, it is possible in a particularly simple manner to subject the specimen fluid, which is mixed with appropriate amino acids for this purpose, to a polymerase chain reaction (PCR), such as described above. In the course of this, the maintenance of appropriate heating and cooling phases can be controlled by the computer arrangement.

The energy source of the computer arrangement is preferably used for impressing the voltage or current. It has been discovered that the net-independent energy source, which is provided anyway in a portable computer arrangement, can simultaneously be used for performing the electrochemical detection process. The net-independent energy source of the portable computer arrangement is in particular an electrical battery or a rechargeable electrical battery.

The temperature-regulating element is preferably a Peltier element.

The computer arrangement preferably has a computer with an input mechanism, in particular with keys, and a display, as well as a supplemental module, which can be connected to a digital interface of the computer and can be connected with the analysis cassette via an analog interface. Digital/analog converters and analog/digital converters, for example, can be attached to the supplemental module. By dividing the computer arrangement into the computer, on the one hand, and the cassette, on the other hand, it is possible in an advantageous manner to install supplemental modules with different electrical requirements for different applications in the same computer provided on site.

The digital interface is preferably a PCMCIA interface (personal computer memory card international association). For example, a corresponding interface of the computer permits the insertion of so-called PCMCIA plug-in cards in the form of debit cards.

In a particularly advantageous manner the computer is a mobile standard computer, in particular a laptop, a notebook, or a computer intended to be held in the hand during operation, for example a palmtop or "hand-held" device. In this embodiment, the division of the computer arrangement into a computer, as well as into a supplemental module becomes clear as being particularly advantageous since, for example, the physician treating a patient on location can use a computer which is provided anyway and which can also take on other tasks. Thus, the investment outlay in the device in accordance with the invention is kept low, and the device becomes particularly suited for application over a broad range.

Preferably, the supplemental module is designed in such a way that it can be at least partially inserted into a housing of the computer. For example, at its end it is in the format of a PCMCIA plug-in card.

The supplemental module also preferably has a recess or opening for inserting the analysis cassette. For example, the supplemental module can be used as a docking station for the analysis cassette.

The above-mentioned temperature-regulating device is preferably placed in the supplemental module. In particular, it is installed there in such a way that it comes into thermal contact over a large area with the inserted or docked analysis cassette.

In accordance with particular embodiments, the device has an electrically operable device for exerting a force on the analysis cassette, which is installed in the supplemental module. This force can be converted into a movement of the working electrode and/or the counter-electrode. This is based on the thought that it is advantageous for the process dependability of the analysis if the working electrode is not yet moistened by the fluid or solution during the heating and cooling phases of the already described PCR. Instead, the working electrode should dip into the fluid or solution only after the PCR for performing the electrochemical analysis is terminated.

In this connection, it is particularly preferred that the device for exerting a force includes an element made of an alloy with shape memory wherein, in particular during heating, the element attempts to return to the manufacture-related original state and generates a force in the process. A known shape memory alloy is Nitinol(™), for example. Shape memory alloys exist, which can be easily deformed at room temperature, but in the course of being heated return to a shape which they had been given during their manufacture by a special treatment.

For heating the shape memory alloy, it is advantageous that it is embodied as a wire or tape, so that because of the resultant electrical resistance it is possible to apply an electrical voltage or an electrical current directly to the wire or the tape.

The device for exerting a force is advantageously arranged in the module in such a way that the device is compressed when the exchangeable cassette is inserted into the recess in the supplemental module. This has the advantage that no separate restoring mechanism is required. The restoring force is instead exerted by the person who plugs or inserts the analysis cassette into the supplemental module.

In accordance with another embodiment, the computer arrangement is designed in such a way that, by employing the detected current signal and/or voltage signal, a diagnosis can be made regarding a pathogen in the fluid or regarding a diseased body cell in the fluid, and this can be shown on the display. The appropriate evaluation is performed by software loaded into the computer, which takes decision data required for detection or diagnosis from a local data bank in the computer arrangement, or from a remote data bank connected by a data net, for example. The connection with the remote data bank can be performed wireless via radio networks, such as WaveLAN, GSM or UMTS.

An analysis cassette embodying features of the present invention is particularly suited for use as an auxiliary or exchange with the above-described device. The analysis cassette for the electrochemical detection of a nucleotide sequence in a fluid has a sealed housing, in which a working electrode with a biopolymer attached to it, which has a specific affinity with the nucleotide sequence to be detected, and a counter-electrode are arranged, wherein the housing has a feeding device without an outlet for taking the fluid to the electrodes in the housing. In an advantageous manner, the analysis cassette can be designed as an expendable cassette, or exchange element, which must be disposed of after a single use.

The analysis cassette, which can be electrically connected to a portable computer arrangement, has the advantage that the wet portion of an electrochemical detection process can be functionally separated from the electronic evaluation portion which is placed in the computer arrangement. Because of this, it is possible in the course of a mobile use on location to perform several different or identical detection processes for a nucleotide sequence present in a fluid sequentially by use of the portable computer arrangement, using different or identical expendable cassettes.

Preferably, the working electrode and the counter-electrode are designed in a way as already explained above in connection with the device. Reference is also made to the explanations already given above in connection with embodiments regarding the adaptation to the portable computer arrangement.

The housing of the analysis cassette preferably has a top section with the working electrode fastened on it, and a bottom section with the counter-electrode.

For the simultaneous detection of several nucleotide sequences which are different from each other, it is possible to provide several working electrodes with biopolymers which are different from each other.

The surface of each working electrode can be coated with the biopolymer and/or soaked in the biopolymer.

Several depressions with a counter-electrode arranged in each are preferably formed in the bottom section of the analysis cassette. In this way, the fluid volume required for analysis can be kept low.

In accordance with a further embodiment, the housing has a compressible area, wherein the working electrode can be moved in a direction toward the bottom section while being compressed by the exertion of a force on the analysis cassette. Such a force can be supplied from the outside, for example by the user. However, in a preferred embodiment this force is exerted by the electrically operable device already described above, which is arranged in the supplemental module. By action of the compression movement, it is possible to keep the fluid from wetting the working electrode during the heating and cooling phases required for the polymerase chain reaction. Only at the end of the temperature-regulation phase is an upper area of the housing moved in a direction toward the bottom section by exerting a force, in the course of which the working electrode comes into contact with the fluid injected into the housing. In this way, the process dependability of the analysis is advantageously increased.

A bellows is preferably provided as the compressible connecting device.

In accordance with another embodiment, the analysis cassette has a storage module, which can be read by the computer arrangement and on which the type of the working electrode, and optionally information regarding the life, the manufacturer and/or the production series are recorded. Thus, the inadvertent mixing up of analysis cassettes with working electrodes intended for different detection purposes can be prevented. For this purpose, the storage module furthermore can only be read, not written on. The data stored in the storage module can be read out by the computer arrangement, for example, by an appropriate contact, and represented on the display.

Preferably, data are also contained in the storage module which define process parameters, in particular process parameters specific to the working electrode. For example, the threshold values for a positive/negative statement regarding the detection are listed for all working electrodes provided in the specific analysis cassette. PCR parameters, such as the number of the PCR cycles which must be run through, for example, can be stored there. DNA sequences of the human genome as a rule are present in bodily fluids in such concentrations that a PCR is simply unnecessary, whereas most viruses require several PCR run-throughs and, therefore, a $2^n$ times repetition for detection. With this information in the storage module it is assured that the device can also evaluate analysis cassettes which had not been defined at the time the device was manufactured. Thus, expensive retrofitting on location by the customer is not necessary and it is possible to react extremely rapidly to actual situations, such as an outbreak of new diseases.

The feeding device without an outlet includes in particular an elastic wall element, which can be pierced with a hollow needle.

Also within the scope of the present invention lies the idea of providing a system of several structurally identical analysis cassettes of the type mentioned, wherein each analysis cassette has one or several working electrodes for detecting one or several nucleotide sequences, and wherein the analysis cassettes differ from one another in that they are suitable for detecting nucleotide sequences which are different from each other, or for detecting combinations of nucleotide sequences which are different from each other. Using such a system of analysis cassettes it is possible in a simple manner for the medical personnel at the location where the patient is, or for a food chemist, to cover a broad spectrum of applications. In other words, it is sufficient if the doctor or chemist has with him a portable computer arrangement, as well as a system of suitable analysis cassettes, which are, for example, approximately only the size of a hand. The analysis cassette can be composed or can be sold, for example, in a common package, together with ampoules containing solutions for specimen preparation, an expendable hypodermic needle, an expendable glove and similar aids, or partial amounts thereof as a "kit of parts".

The different analysis cassettes are preferably prepared for different diagnoses regarding a pathogen in the fluid or regarding a diseased body cell in the fluid. For example, an analysis cassette is designed for detecting influenza and has an appropriate label. Such a cassette has working electrodes for detecting different viral strains, for example.

In accordance with a particularly preferred further embodiment, different analysis cassettes are prepared for a hierarchic process in regard to their potential diagnostic results. For example, at least a first analysis cassette is provided for a rough diagnosis, and is followed by one or several further analysis cassettes for exact diagnosis, wherein the further analysis cassettes should be optionally selected as a result of the rough diagnosis. For example, a rough classification as to viruses or bacteria as the causes of the illness is provided by the first analysis cassette, after which the exact type of the pathogen is detected by further analysis cassettes of other types, if necessary.

A supplemental module for connection with a digital interface of a portable computer embodying features of the present invention includes an analog interface for connection with an exchangeable analysis cassette, having an electronic circuit arrangement which is designed for impressing a voltage and/or a current on electrodes in the analysis cassette and to condition a current or voltage signal created as a result of an electrochemical reaction in the analysis cassette, and a temperature-regulating element for cooling and/or heating a fluid introduced into the analysis cassette, wherein the supplemental modules can be connected to the computer in such a way that the temperature-regulating element can be fed from the energy source of the computer.

An amplifier and/or an A/D converter, for example, are provided for signal conditioning.

Preferably, the supplemental module is embodied without its own or without an installed display device. The display device, for example the monitor or the display of the portable computer, can be used for representing a measuring result.

The explanations provided above in connection with the analysis cassettes and devices in accordance with the invention also analogously apply to advantages and preferred embodiments of the supplemental module, the portable computer, the digital interface, the analysis cassette and the electrodes.

Preferably, the supplemental module can be connected to the portable computer in such a way that the energy required for impressing the voltage and/or the current can be taken from the energy source of the computer, in particular a battery or a rechargeable battery.

For a compact design, the supplemental module can have a recess for inserting the analysis cassette. In view of this compact design, it is also advantageous that the interface is a PCMCIA interface.

In accordance with a further embodiment, the temperature-regulating element comes into thermal contact with the analysis cassette over a large area. By the use of the temperature-regulating element, which can preferably be controlled from the portable computer for performing several heating and cooling phases, it is possible to trigger a polymerization chain reaction in a fluid located in the analysis cassette.

The temperature-regulating element is preferably a Peltier element.

Moreover, the supplemental module preferably has an electrically operable device for exerting a force on the analysis cassette. Reference is made to the explanations made above regarding the purpose, the advantages and preferred embodiments of this device.

The recognition that the described analysis cassette can be produced in a simple manner by the following process also lies within the scope of the present invention: a) a molded plastic part is produced, preferably by compression molding; b) several working electrodes are fastened to the molded plastic part; (c) several counter-electrodes are attached to the molded plastic part; (d) the working electrodes are dipped, suspended from the molded plastic part, into different fluids containing specific biopolymers; (e) the molded plastic part is folded in such a way that the working electrodes come to lie above associated counter-electrodes; and (f) wall elements of the plastic molded part which come to rest on each other are glued or welded together and a sealed housing of the analysis cassette is formed.

This method can also be used for producing analysis cassettes other than those for the electrochemical detection of a nucleotide sequence in a fluid.

With methods embodying features of the present invention, the molded plastic part is preferably produced with several depressions, wherein for each counter-electrode one depression is provided in particular.

Analysis cassettes can be produced cost-effectively in large numbers by this production method, wherein the steps (a) to (c) as well as (e) and (f) can also be uniformly executed for analysis cassettes which are intended to be readied for different detection purposes. This means, for example, that a top section and a bottom section of the molded plastic part can be cost-effectively produced in large numbers in only one variation. Only in the subsequent process step (d) of the insertion or soaking of the working electrodes are the analysis cassettes adapted to their subsequent purpose, so that it is possible to react rapidly to actual requirements, or that smaller numbers can also be cost-effectively produced for special purposes.

Exemplary embodiments of the device in accordance with the invention, the analysis cassette, the supplemental module, as well as the production process will be explained in greater detail by reference to FIGS. 1 to 7 in what follows.

Figure 1:
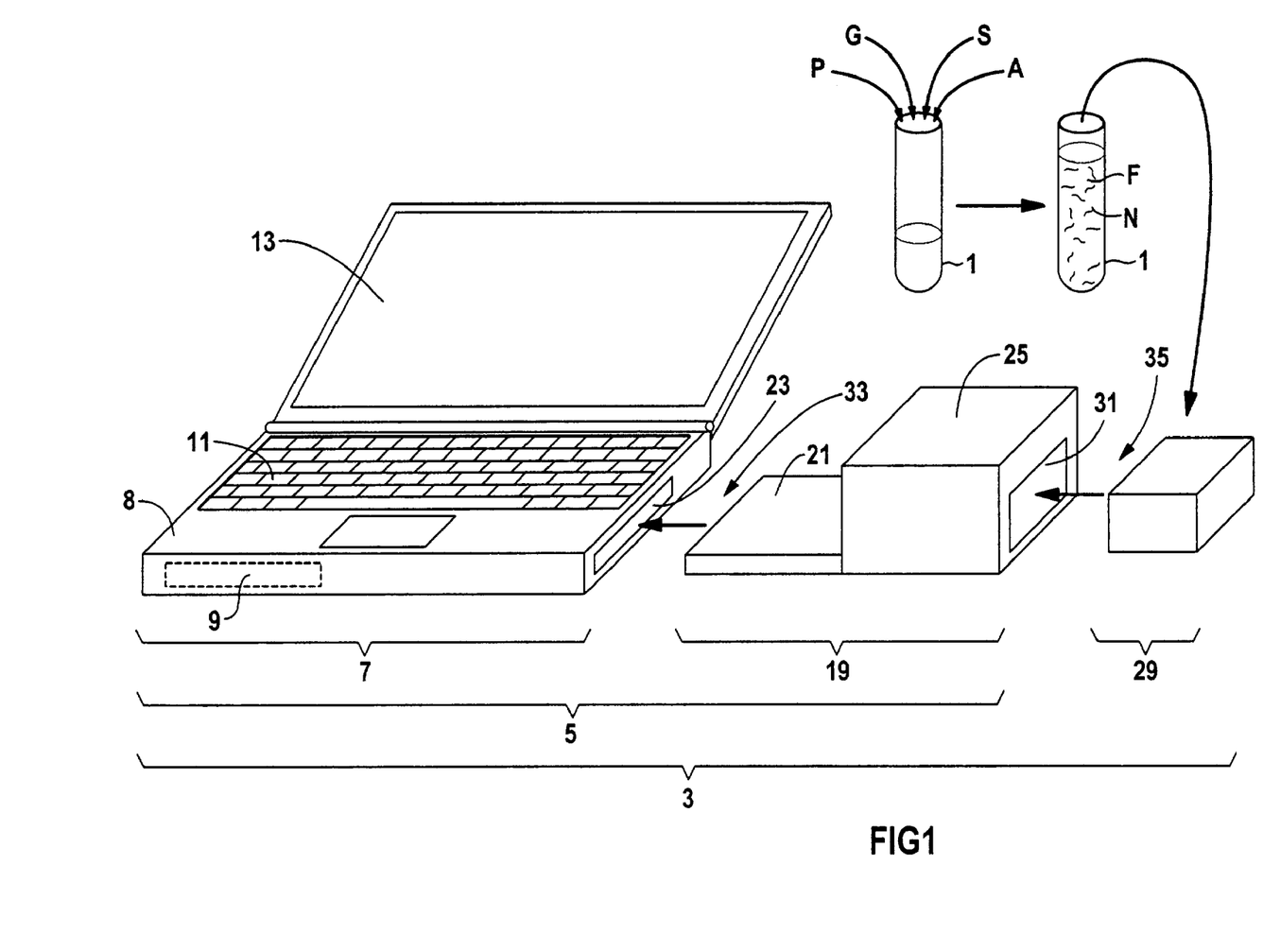
FIG. 1 shows a schematic and perspective view of a device embodying features of the present invention.

FIG. 1 shows how a specimen P, for example a blood sample, together with an anticoagulant G and, if required, a substance which breaks cell walls open, are placed in a vessel 1. A special enzyme S is added, which cuts the DNA strands or nucleotide sequences released after the cell walls have been broken open at exactly predetermined locations ("enzymatic scissors"). Moreover, amino acids A are added for subsequently performing a polymerase chain reaction and in this way to achieve a multiplication of the DNA sections or nucleotide sequences N in the fluid F. The DNA sequences can come from viruses, bacteria or cancer cells. They can furthermore also come from "normal" cells in the human body, so that information regarding the human genome can also be obtained, for example indications of an inherited disease or of a predisposition to certain illnesses in the course of life.

A device 3, which includes a portable computer arrangement 5 with a collapsible mobile standard computer 7, is provided for the electrochemical detection of the nucleotide sequences N contained in the fluid F. A battery or rechargeable battery is provided as the energy source 9 in a housing 8 of the computer 7. Furthermore, a keyboard 11 for user input, as well as a pivotable display 13 for representing the detection results or a diagnosis are furthermore contained in the housing 8. At times, the rechargeable battery can be connected to a network or charging element (not shown).

The device 3 further includes a supplemental module 19, which can be inserted with a flat plug element 21 into an opening 23 in the housing 8 of the computer 7. The supplemental module 19 has a thicker receiving element 25 for receiving an analysis cassette 29 ("cartridge") designed as an expendable cassette, which is also a component of the device 3. For docking the analysis cassette 29 to the receiving element 25, the latter has a recess 31.

The electrical connection of the supplemental module 19 with the computer 7 takes place via a digital interface 33 embodied as a PCMCIA interface 33. The connection is made by inserting the plug element 21 into the opening 23, whereupon corresponding plug contacts are closed and in the course of which a connection of the supplemental module 19 with the energy source 9 is also made.

The electrical coupling of the analysis cassette 29 to the supplemental module 19 takes place via an analog interface 35, whose plug connection is made when the analysis cassette 29 is docked in the recess 31.

Figure 2:
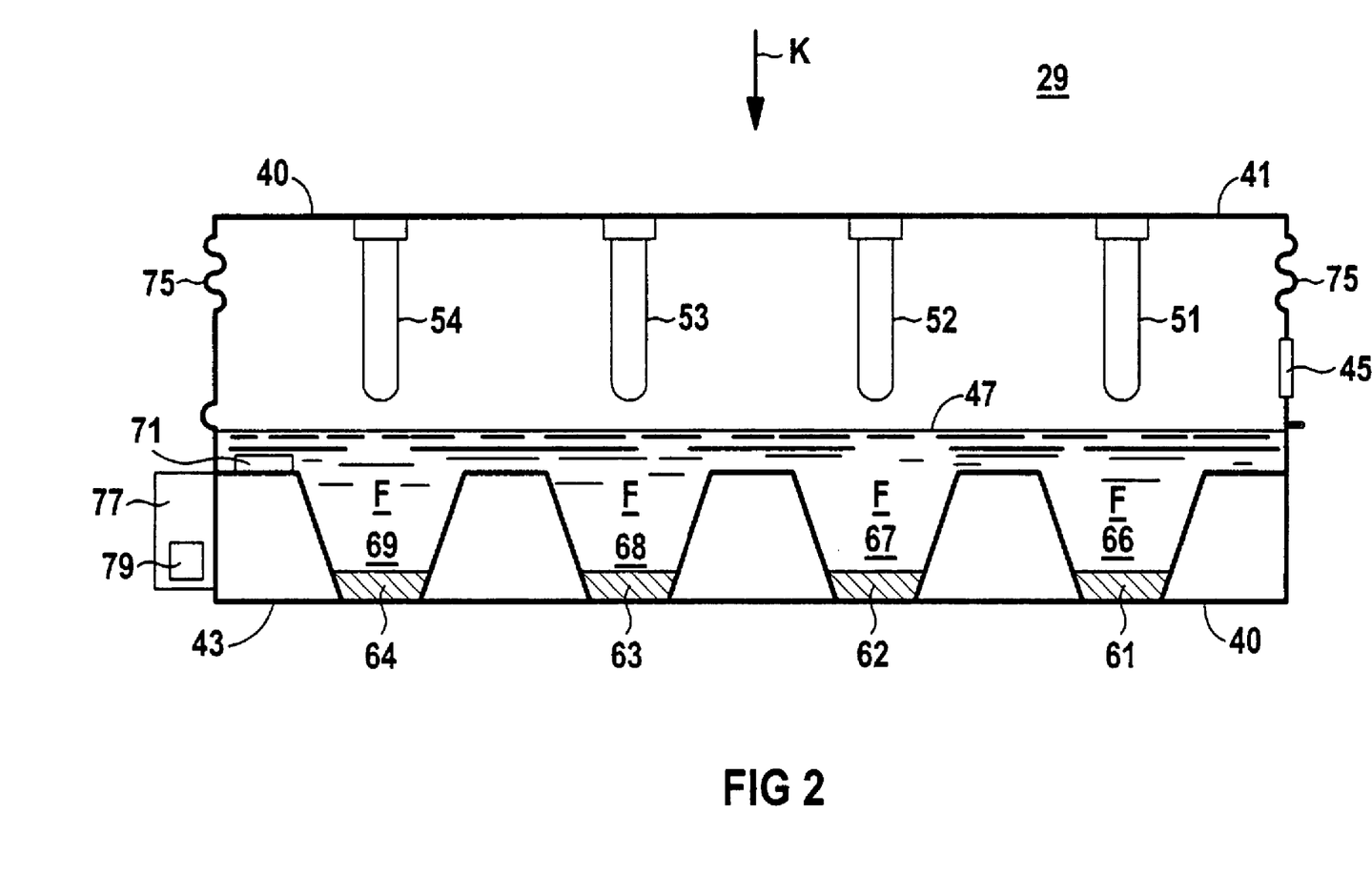
FIG. 2 shows a detailed view in longitudinal section of the analysis cassette of the device shown in FIG. 1.

The analysis cassette 29 of the approximate size of a matchbox is shown in detail in FIG. 2. It includes a fluid-tight housing 40 with a cover-like top section 41 and a trough-like bottom section 43. The housing is made of plastic, for example, in accordance with the production method which will be further described below. Preferred dimensions of the analysis cassette 29 are approximately 50 mm×35 mm×12 mm (thickness). Product variants with a smaller cassette are also possible.

An elastic wall element 45 is integrated in a left wall element of the top section 41, and can be pierced by a hollow needle for introducing a few microliters of the fluid F into the housing 40. For example, the wall element 45 is a membrane which can be pierced, such as is used in connection with infusion bottles. The prepared fluid F was inserted by a hypodermic needle into the interior of the analysis cassette 29, into its analysis chamber, up to a level 47.

In place of the elastic wall element 45, other devices, for example valve-based feed devices, can be provided, which prevent the inserted fluid F from flowing back out of the analysis chamber. It is desirable that the analysis cassette, which is embodied as an expendable item, is tightly sealed during delivery, which results in good storage capabilities, even under the highest hygienic demands.

An electrode system for performing the electrochemical detection method, which contains four working electrodes 51, 52, 53, 54, attached to the top section 41, four gold-plated counter-electrodes 61, 62, 63, 64, attached to the bottom section 43, as well as a common reference electrode 71, is located in the interior of the analysis cassette 29. The flat counter-electrodes 61, 62, 63, 64 are positioned in the bottom in depressions 66, 67, 58, 69, which were created by the shaping of the bottom section 43.

The rod-like working electrodes 51, 52, 53, 54, made of a carbon fiber material, or another material known per se for this purpose, are coated with different biopolymers, which have different affinities for the nucleotide sequences N in the fluid F. The biopolymers or receptor molecules function as matching "counterpieces" to the nucleotide sequences to be detected. If the appropriately prepared working electrodes 51, 52, 53, 54 are brought into contact with the fluid F, exactly matching nucleotide sequences are exclusively deposited on them, so that thereafter the deposit can be detected by an electrical evaluation. A method suitable for this is the so-called PSA (potentiometric stripping analysis). For this purpose, an electrical current is impressed between each one of the working electrodes 51, 52, 53, 54 and each one of the associated counter-electrodes 61, 62, 63, 64, and thereafter a slowly rising voltage between the respective working electrode 51, 52, 53, 54 and the reference electrode 71 is measured. If nucleotide sequences N of the type to be detected have been deposited on the working electrode 51, 52, 53, 54, a pause of the voltage increase at 0.8 V can be observed, since at this voltage the guanine contained in the DNA section to be detected oxidizes. The chronological width of this voltage plateau is a measure of the oxidized amount of guanine. A conclusion can be drawn from this as to whether DNA segments of the type in question were present in a diagnostically relevant amount in the tested specimen.

A bellows 75 extending around the top section 41 is integrated into it, so that the lowering of the working electrodes 51, 52, 53, 54 below the level 47 can be achieved by exerting an external force K from above on the top section 41.

An electrical contact block 77 is provided on the right side of the housing 40, which is also used as a holder for a storage module 79 embodied as an electronic identification chip. Data relating to the type of working electrode, a definite serial number, only issued once, as well as additional information regarding the manufacturer, the manufacturing date, the service life remaining, etc., as well as electrode-specific process parameters can be read out by the computer arrangement 5 from the read-only (by the final consumer) storage module 79.

Figure 3:
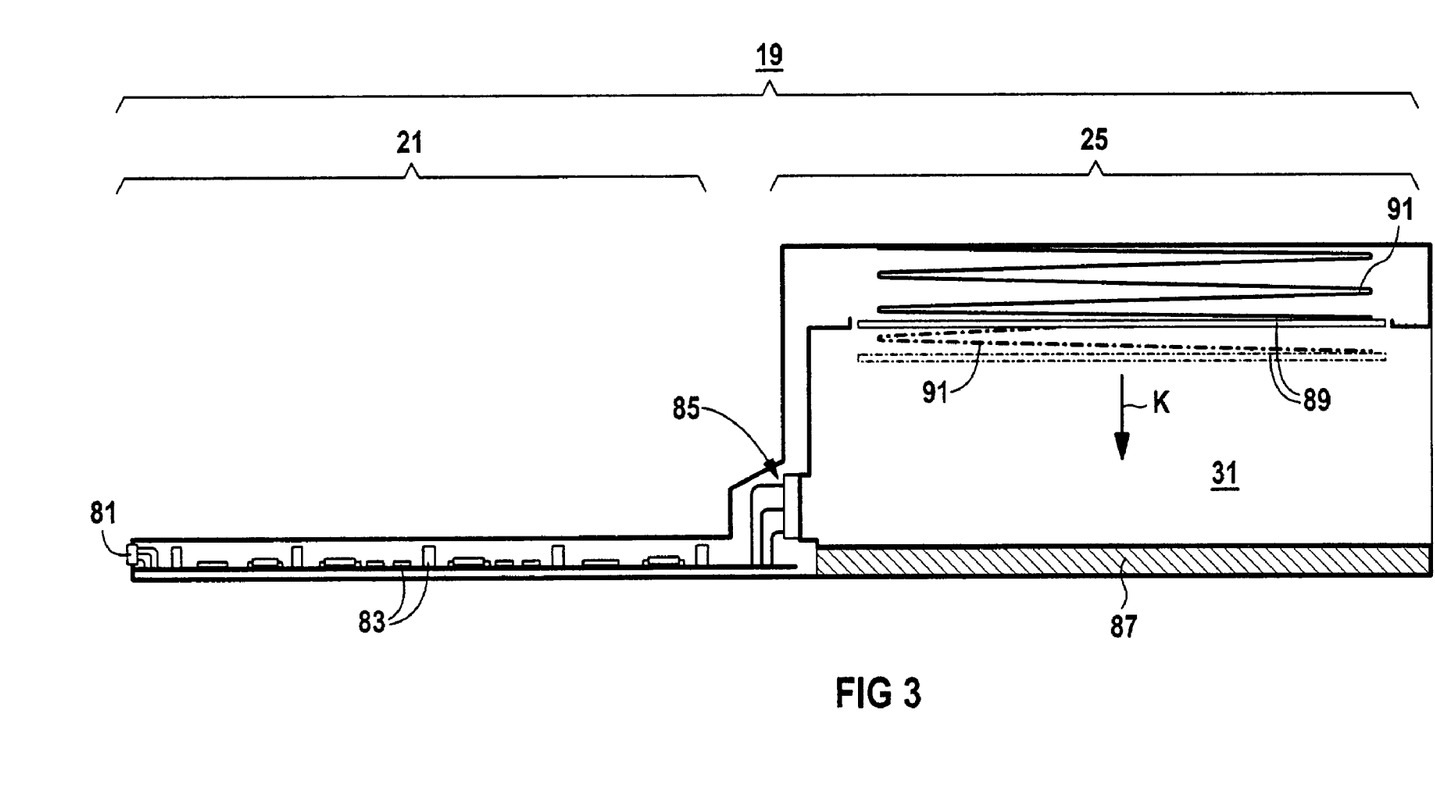
FIG. 3 shows a detailed view in longitudinal section of the supplemental module of the device shown FIG. 1.

The supplemental module 19 in accordance with the invention, which is made with a light plastic housing, is shown in greater detail in FIG. 3. The supplemental module 19 has a plug connection 81 on its plug element 21 on its end for connecting it with the digital interface 33 of the portable computer 7. An electronic circuit arrangement 83 is provided in the interior of the plug element 21 which comprises, inter alia, specific electronic components required for performing the electrochemical analysis, such as an A/D converter, electrical current sources or voltage sources and current or voltage meters. A Peltier element 87 is integrated into the bottom of the receiving element 25, which protrudes from the computer 7 and is therefore accessible to the user and makes the repeated controlled heating and subsequent cooling required for the PCR possible. Electronic components for controlling the Peltier element 87 are housed in the plug element 21. The computer 7 provides the energy supply to the Peltier element 87 and takes on the control of the chronological course of the temperature.

The analysis cassette 29 in FIG. 2 can be inserted from the left side into the recess 31 of the supplemental module 19, until its contact block 77 snaps into a plug connector 85. Because of this snapping in, the plug connector 85 is used as a holding device for the analysis cassette 29. By making the plug connection, the electrodes 51, 52, 53, 54, 61, 62, 63, 64 in the interior of the analysis cassette 29 are connected with the electronic circuit arrangement 83 in the supplemental module 19.

The electronic components in the supplemental module 19 for performing the electrochemical analysis, in particular the components provided for conditioning and possibly evaluation, are electromagnetically shielded, for example, by one or several sheet metal plates and/or a Faraday cage.

Special and separate ground conductors are provided for the interference-free separation of the supplemental module 19, or its electronic components, from the computer 7. With the same aim, optical couplers can be provided for signal transmission.

Figure 4:
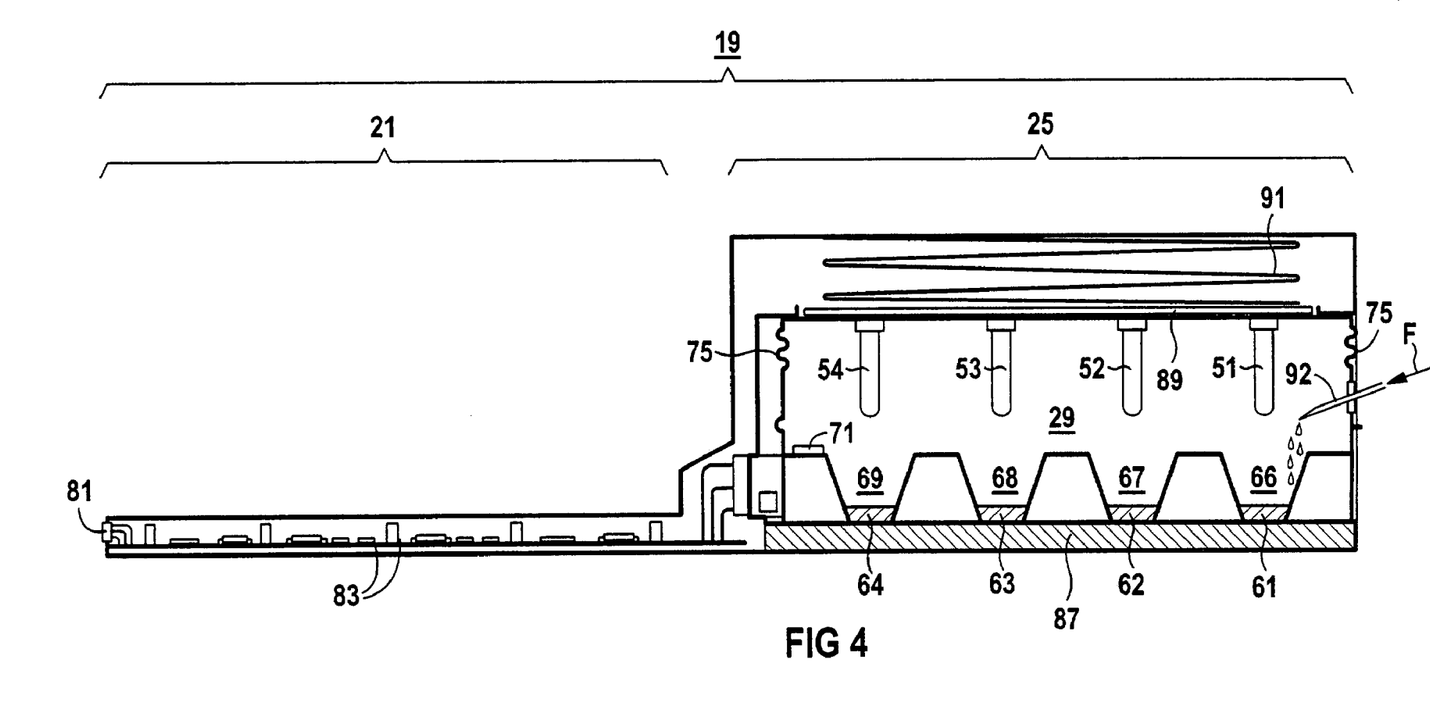
FIG. 4 shows the supplemental module from FIG. 3 with the analysis cassette from FIG. 2 inserted.

The supplemental module 19, together with the inserted analysis cassette 29, is represented in FIG. 4. In the course of inserting the analysis cassette 29 into the recess 31, a plate 89 arranged on the top of the recess 31 in the receiving element 25 was pushed out of its position represented by dashed lines in FIG. 3 and upward against the force of a shape memory element 91. The shape memory element 91 is produced in the form of a meander-shaped metal tape made of SMA (shape memory alloy, for example Nitinol(™)). The electrical resistance of the metal tape is used at the end of the PCR for heating the metal tape by applying an electrical voltage or impressing an electrical current. Because of this, the shape memory element 91 seeks to return to its original shape which had been impressed on it in the course of its manufacture by a special treatment. In the course of this attempt to return to the original shape, the plate 89 connected with the shape memory element 91 generates the external force K (see FIG. 3), so that the bellows 75 is compressed and the working electrodes 51, 52, 53, 54 dip into the fluid F, which had previously been injected into the analysis chamber by a hollow needle 92 through the elastic wall element 45.

Thus, the operation of the device 3 is performed in the following steps:

1. Preparation of a specimen P from a fluid F;
2. Docking of the desired analysis cassette 29 at the computer arrangement 5;
3. Performing the polymerase chain reaction by use of the Peltier element 87 to the extent necessary;
4. Dipping the electrodes 51, 52, 53, 54 into the fluid F by activating the shape memory element 91; and
5. Electrochemical detection by PSA or DPV (differential pulsed voltametry).

Figure 5:
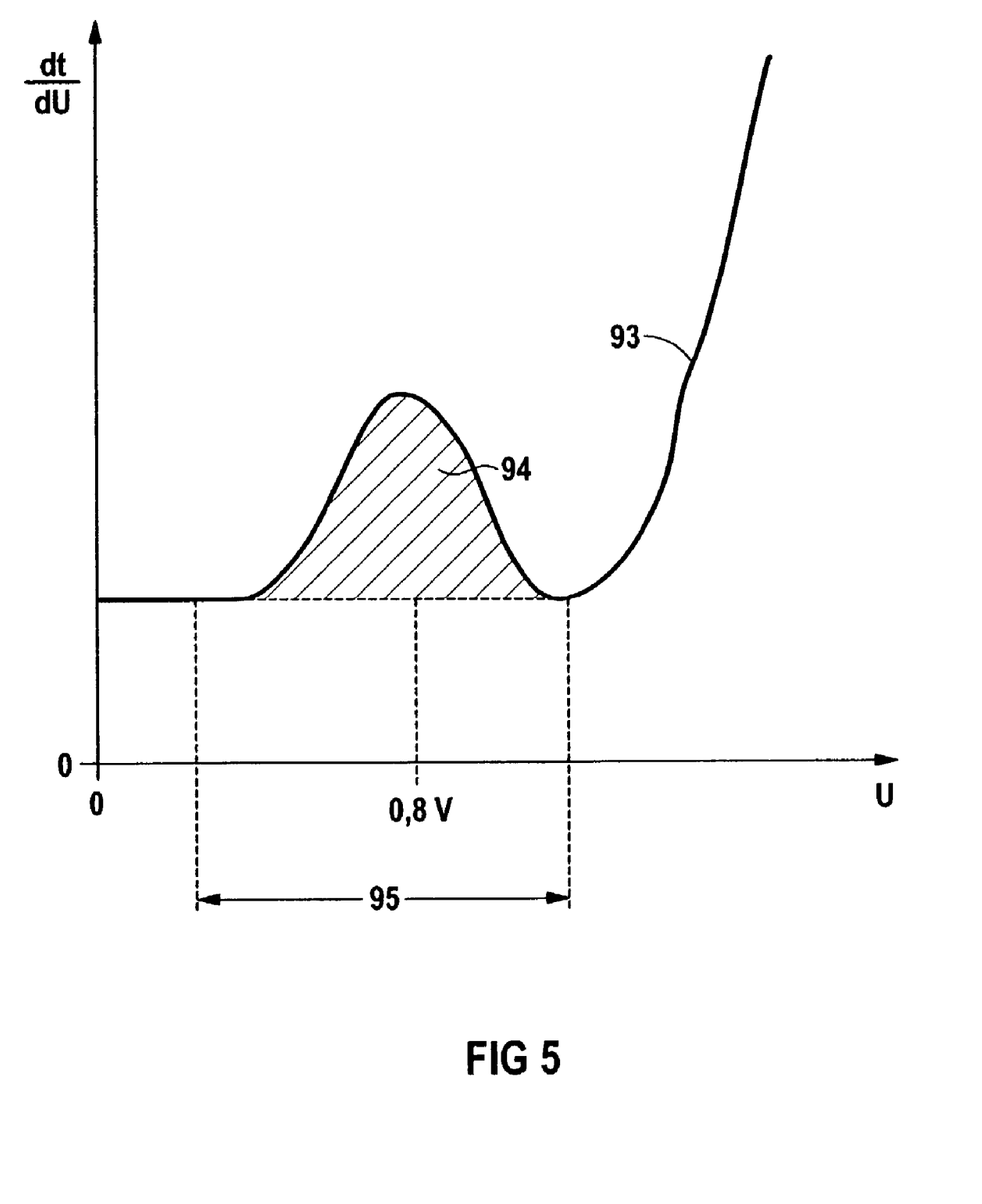
FIG. 5 shows a signal course which can be detected by the device shown in FIG. 1.

A curve 93, such as results in the course of the electrochemical analysis, is represented by way of example in FIG. 5. In the example, a very low constant current in the range between 1 pA and 1 nA was fed between a working electrode and a counter-electrode, and the chronological course U(t) of the voltage between the reference electrode and the working electrode was recorded. Subsequently, the derivative dt/dU was formed, which led to the curve 93. In case of a deposition of DNA fragments of the sought-after type on the working electrode, a clear maximum in the range of 0.8 V is shown because of the oxidation of guanine, wherein the surface 94 below the maximum is proportional to the amount of guanine. In the case of a PSA, shown by way of example in FIG. 5, a measuring range 95 is represented, which is adjoined on the left side by a redox area and on the right side by an electrolysis area.

As an alternative to the PSA as a galvanostatic process it is possible to employ a potentiostatic process, preferably DPV. Potentiostatic processes are clearly more robust in connection with interferences, and therefore provide a better signal/noise ratio in actual use. In contrast to "galvanostats," which are exited by a constant current, "potentiostats" operate with a constant voltage.

For example, a step-by-step rising voltage potential in the range between approximately 0.6 V to 1.2 V is impressed on the measuring cell between the reference electrode and the counter-electrode by a controllable low-ohmic voltage source. The current which runs off to ground via the working electrode is measured at each voltage step and over a defined length of time. The course of the curve of the signal obtained corresponds to the PSA (see FIG. 5), if dt/dI is entered on the y-axis, and the current I on the x-axis.

It is also possible to measure several working electrodes in parallel in a single measuring operation by a current meter assigned to each respective electrode. In other words, if each electrode is assigned its own ammeter, it is possible to evaluate all working electrodes parallel in one measuring operation. Limits are set here only by the total current flowing through the analysis cassette 29, and the data pickup speed of the electronic device used. This represents an immense time advantage over the solutions, often employed in the laboratory, with multiplexers for switching between the electrodes and sequential processing of all electrodes, since a measuring cycle takes at least approximately 45 sec.

Figure 6:
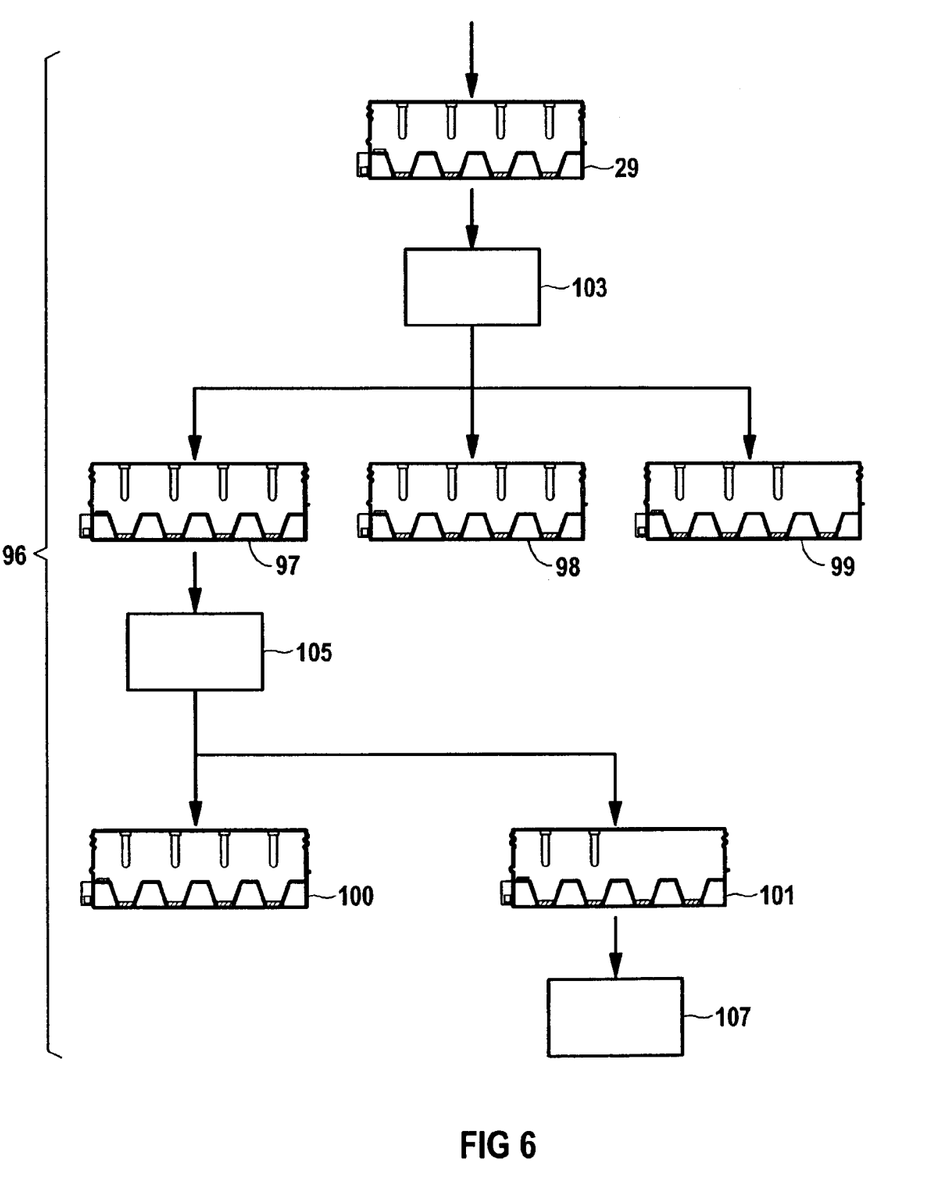
FIG. 6 shows a schematic representation of a system of analysis cassettes, as well as their use in a hierarchical way.
Figure 7:
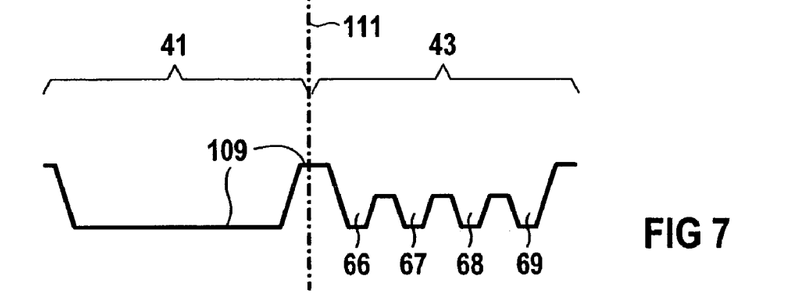
FIGS. 7 to 11 show examples of a production method embodying features of the present invention.

A system 96 of several analysis cassettes 29, 97, 98, 99, 100, 101, which are structurally identical, so that they can all be inserted into the supplemental module 19, is schematically represented in FIG. 6. The analysis cassettes 29, 97, 98, 99, 100, 101 differ from each other in that they are suitable for detecting nucleotide sequences N, which differ from each other, or for detecting combinations of nucleotide sequences N, which differ from each other. In the example, a detailed detection process is started by using a first analysis cassette 29, which results in a rough diagnosis 103 being shown on the display 13. Furthermore, as a function of the result of the rough diagnosis 103, the user is shown on the display 13 which analysis cassette 97 should next be inserted into the supplemental module 19 for a possibly desired fine diagnosis 105. The fine diagnosis 105 is also represented on the display 13. The hierarchical use of the analysis cassettes 29, 97, 98, 99, 100, 101 is also indicated in FIG. 6 in connection with a subsequent ultrafine diagnosis by the analysis cassette 101.

A cost-effective manufacturing process for the analysis cassette 29 is illustrated in FIGS. 7 to 11. The process is started (FIG. 7) by the compression molding of a molded plastic part 109, in which the top section 41 and the bottom section 43 of the housing 40 are combined into one piece. The aim of the manufacturing process is to produce the analysis cassette 29 in the manner of a foldable blister pack. To assure folding, the molded plastic part 109 can be bent along a center plane 111.

Figure 8:
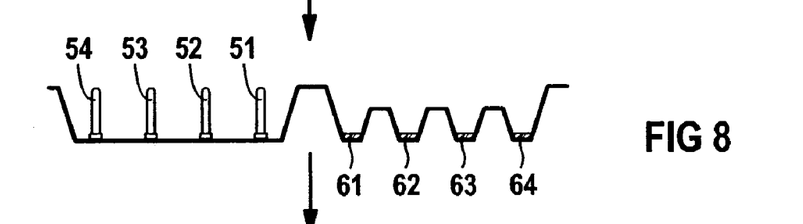
Figure 9:
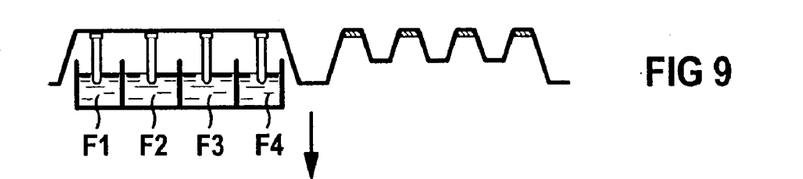
Figure 10:
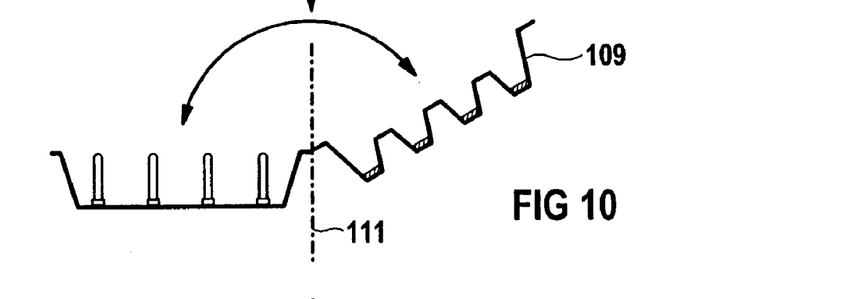

Prior to bending, first the working electrodes 51, 52, 53, 54, as well as the associated counter-electrodes 61, 62, 63, 64, are attached in a second step (FIG. 8). Thereafter, in the third step (FIG. 9) the working electrodes 51, 52, 53, 54, suspended from the molded plastic part, are dipped into different baths containing different specific biopolymers in fluids F1, F2, F3, F4, until a sufficient coating or wetting has been achieved.

Figure 11:
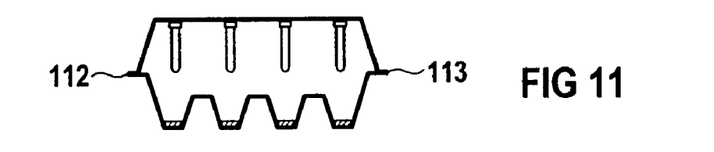

Following this (FIG. 10), the molded plastic part 109 is folded in such a way that the working electrodes 51, 52, 53, 54 come to lie above the associated counter-electrodes 61, 62, 63, 64. After folding, the top section 41 and the bottom section 43 are tightly glued or welded by ultrasound at the edges 112, 113 in a last step (FIG. 11). This results in good storage capabilities, even under adverse storage and climatic conditions.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art and remain within the scope of the appended claims and their equivalents.

What is claimed is:

1. A device for the electrochemical detection of a nucleotide sequence in a fluid comprising:
    a working electrode attached to a top section of a molded plastic part;
    a counter-electrode attached to a bottom section of the molded plastic part, wherein the working electrode is attached to a biopolymer that has a specific affinity with the nucleotide sequence to be detected and the molded plastic part is foldable in such a way that the working electrode comes to lie above the counter electrode and wall elements of the top and bottom sections of the molded plastic part are connected to one another to form a sealed fluid tight housing of an exchangeable analysis cassette;
    the exchangeable analysis cassette formed being operable to accept the introduction of the fluid and having the working electrode and the counter-electrode arranged within the sealed fluid tight housing of the analysis cassette and can be contacted with the fluid, the sealed fluid tight housing comprising a compressible area such that an exertion of a force on the analysis cassette after assembly moves the working electrode and the counter electrode toward each other within the sealed fluid tight housing;
    a portable computer arrangement electrically connected with the analysis cassette comprising a display and an energy source, the energy source being independent of an electrical supply net, wherein at least one of a voltage and a current can be impressed on at least one of the working electrode and the counter-electrode; wherein at least one of a current and a voltage signal can be detected as a consequence of the nucleotide sequence to be detected being deposited on the working electrode; and wherein a detection result can be represented on the display; and
    a temperature-regulating element for cooling and/or heating the fluid in the analysis cassette, the temperature-regulating element being fed from the energy source.

2. The device of claim 1 wherein at least one of the voltage and the current can be impressed by employing the energy source to facilitate a potentiometric stripping analysis and the analysis cassette comprises a valve-based feed device operable to prevent fluid introduced into the analysis cassette from flowing back out of an analysis chamber.

3. The device of claim 1 wherein the temperature-regulating element is a Peltier element operable to perform several heating and cooling phases of the fluid to facilitate a polymerase chain reaction and the analysis cassette further comprising an common reference electrode located within the interior of the sealed fluid tight housing.

4. The device of claim 1 wherein the computer arrangement comprises a computer having an input device and a display, and a supplemental module, which can be connected to a digital interface of the computer and can be connected with the analysis cassette via an analog interface and the bottom section of the molded plastic part is configured as a trough to collect the fluid inserted into the sealed fluid tight housing and position the fluid collected over the counter-electrode.

5. The device of claim 4 wherein the digital interface is a PCMCIA interface.

6. The device of claim 4 wherein the computer is a mobile standard computer selected from the group consisting of a laptop, a notebook, and a palmtop computer.

7. The device of claim 4 wherein the analysis cassette has at least one wall comprising a feeding device without an outlet operable to permit the introduction of the fluid into the sealed fluid tight housing of the analysis cassette, the feeding device without an outlet being an elastic wall that can be pierced with a hollow needle for introducing the fluid into the analysis cassette.

8. The device of claim 4 wherein the supplemental module defines a recess wherein the analysis cassette can be inserted, and compression movement of the compressible area is operable to keep the fluid from wetting the working electrode during the heating and cooling phases required for the polymerase chain reaction, the compressible area being a bellows integrated into a wall of the molded plastic part.

9. The device of claim 4 wherein the temperature-regulating element is arranged in the supplemental module such that it may be brought in thermal contact with the analysis cassette over a large surface.

10. The device of claim 4 further comprising an electrically operable device that exerts the force on the analysis cassette and that is arranged in the supplemental module, the force being converted into a movement of the working electrode and/or the counter electrode such that the working electrode is not moistened by the fluid during heating and cooling phases associated with a polymerase chain reaction.

11. The device of claim 10 wherein the electrically operable device that exerts the force comprises an element comprised of a shape memory alloy, wherein the element is biased towards returning to an original state thereby generating the force.

12. The device of claim 10 wherein the electrically operable device that exerts the force is arranged in the supplemental module such that the analysis cassette is compressed in the course of inserting the analysis cassette in the recess of the supplemental module.

13. The device of claim 1 wherein the computer arrangement is configured such that by employing at least one of the detected current signal and the detected voltage signal, a diagnosis can be made regarding at least one of a pathogen in the fluid and a diseased body cell in the fluid after at least one amino acid is mixed with the fluid.

14. An analysis cassette for the electrochemical detection of a nucleotide sequence in a fluid comprising:
  a sealed fluid tight housing in which a working electrode and a counter-electrode are arranged, the working electrode and the counter-electrode being located within the interior of the sealed fluid tight housing, the sealed fluid tight housing configured from a molded plastic part having a top section and a bottom section, the top section being attached to the working electrode and the bottom section being attached to the counter-electrode, the sealed fluid tight housing being formed by folding the molded plastic part such that the working electrode comes to lie above the counter-electrode in the interior of the sealed fluid tight housing, wherein:
  the working electrode has a biopolymer attached thereto, which has a specific affinity with the nucleotide sequence to be detected; and
  wherein the sealed fluid tight housing comprises (1) a feeding device without an outlet integrated within a first wall of the sealed fluid tight housing for introducing the fluid to the counter electrode within the interior of the sealed fluid tight housing and (2) a bellows integrated within the first wall and/or a second wall of the sealed fluid tight housing such that by an exertion of a force on the sealed fluid tight housing the working electrode is moved during compression of the bellows toward the counter electrode.

15. The analysis cassette of claim 14 wherein the sealed fluid tight housing comprises a top section with the working electrode connected thereto, a bottom section with the counter-electrode connected thereto, and a reference electrode, and wherein the working electrode, the counter-electrode, and the reference electrode are located within the interior of the sealed fluid tight housing.

16. The analysis cassette of claim 14 comprising a plurality of working electrodes, each of which is attached to a different biopolymer.

17. The analysis cassette of claim 15 wherein an outer wall of the bottom section comprises a plurality of depressions, each of which has counter-electrode arranged therein.

18. The analysis cassette of claim 15 wherein the working electrode can be moved into the fluid in the bottom section during compression of the bellows.

19. The analysis cassette of claim 14 comprising a storage module, which can be read by a computer arrangement, wherein type of working electrode and, optionally, information regarding at least one of storage capability, manufacturer, and production series are recorded.

20. The analysis cassette of claim 14, wherein the feeding device without an outlet comprises an elastic wall element that be pierced by a hollow needle.

21. A system of analysis cassettes comprising a plurality of analysis cassettes, wherein each analysis cassette of the plurality comprises at least one working electrode for detecting at least one nucleotide sequence deposited on the at least one working electrode via an electrochemical process facilitated by at least one heating and cooling cycle of a fluid, wherein the analysis cassettes differ from one another in that each is configured for detecting at least one of a particular nucleotide sequence and a combination of nucleotide sequences, wherein the particular nucleotide sequence and the combination of nucleotide sequences differ from one another, and wherein at least one of the plurality of analysis cassettes comprises a sealed fluid tight housing, the sealed fluid tight housing configured from a molded plastic part having a top section and a bottom section, the top section being attached to the at least one working electrode and the bottom section being attached to a counter electrode, the sealed fluid tight housing being formed by (1) folding the molded plastic part such that the at least one working electrode comes to lie above the counter electrode on the interior of the sealed fluid tight housing and (2) bonding a first wall element of the top section to a second wall of the bottom section, the sealed fluid tight housing having a compressible area such that an exertion of a force on the sealed fluid tight housing after assembly moves the at least one working electrode and the counter electrode toward each other.

22. The system of claim 21 wherein the analysis cassettes are configured for different diagnoses regarding a pathogen in the fluid or a diseased body cell in the fluid, and the exertion of the force on the sealed fluid tight housing is generated by a device that includes an element made from a shape memory alloy that attempts to return to the manufacture-related original state during heating.

23. The system of claim 22 wherein the analysis cassettes are configured for a hierarchical process based on their potential diagnostic results.

24. The system of claim 23 wherein at least one analysis cassette is configured to provide a rough diagnosis, and at least one additional analysis cassette is configured to provide a fine diagnosis, and wherein optionally the at least one additional analysis cassette is selected based on a result of the rough diagnosis.

* * * * *